(12) United States Patent
Kawasaki

(10) Patent No.: US 7,943,623 B2
(45) Date of Patent: May 17, 2011

(54) PHARMACEUTICAL COMPOSITION COMPRISING 2,3-DIHYDRO-6-NITROIMIDAZO [2,1-B] OXAZOLE DERIVATIVES

(75) Inventor: Junichi Kawasaki, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 543 days.

(21) Appl. No.: 11/996,699

(22) PCT Filed: Jul. 19, 2006

(86) PCT No.: PCT/JP2006/314708
§ 371 (c)(1),
(2), (4) Date: Jan. 24, 2008

(87) PCT Pub. No.: WO2007/013477
PCT Pub. Date: Feb. 1, 2007

(65) Prior Publication Data
US 2010/0130508 A1    May 27, 2010

(30) Foreign Application Priority Data
Jul. 28, 2005 (JP) .................. 2005-218563

(51) Int. Cl.
*A61K 31/497* (2006.01)
*A61K 31/47* (2006.01)
*A61K 31/445* (2006.01)
*A61K 31/42* (2006.01)

(52) U.S. Cl. .................. 514/254.02; 514/312; 514/322; 514/375

(58) Field of Classification Search ............. 514/254.02, 514/312, 322, 375
See application file for complete search history.

(56) References Cited

U.S. PATENT DOCUMENTS
7,262,212 B2    8/2007    Tsubouchi et al.

FOREIGN PATENT DOCUMENTS
| EP | 0 901 786 A2 | 3/1999 |
|---|---|---|
| EP | 1 553 088 A1 | 7/2005 |
| JP | 2004-149527 A | 5/2004 |
| WO | 03/063833 A1 | 8/2003 |
| WO | 2005/042542 A1 | 2/2005 |

OTHER PUBLICATIONS

Kuppuswamy Nagarajan, et al.: Nitroimidazoles XXI 2,3-dihydro-6-nitroimidazo[2,1-b] oxazoles with antitubercular activity; Eur. J. Med. Chem 24 (1989) 631-633.

Dilip R. Ashtekar, et al.: In Vitro and in Vivo Activities of the Nitroimidazole CGI 17341 against *Mycobacterium tuberculosis*; Antimicrobial Agents and Chemotherapy, Feb. 1993, p. 183-186; vol. 37, No. 2.

*Primary Examiner* — Raymond J Henley, III
(74) *Attorney, Agent, or Firm* — Sughrue Mion, PLLC

(57) ABSTRACT

A pharmaceutical composition according to the present invention comprises: (I) at least one member selected from the group consisting of oxazole compounds, optically active isomers thereof, and salts thereof, the oxazole compounds being represented by general formula (1): wherein $R^1$ represents a hydrogen atom or $C_{1-6}$ alkyl group; n represents an integer from 0 to 6; and $R^2$ represents, for example, a group of general formula (A) shown below: wherein $R^3$ represents a phenoxy group, optionally substituted on the phenyl ring with one or more members selected from the group consisting of halogen atoms, halo-substituted or unsubstituted $C_{1-6}$ alkyl groups, and halo-substituted or unsubstituted $C_{1-6}$ alkoxy groups; and (II) at least one cellulose compound selected from the group consisting of hydroxypropyl methylcellulose phthalate and hydroxypropyl methylcellulose acetate succinate. The present pharmaceutical composition has an improved oxazole compound water solubility.

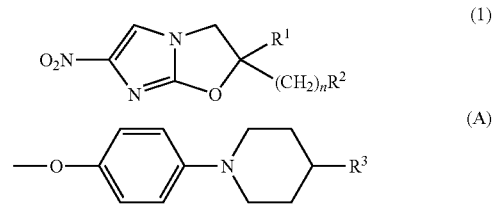

17 Claims, 1 Drawing Sheet

PHARMACEUTICAL COMPOSITION COMPRISING 2,3-DIHYDRO-6-NITROIMIDAZO [2,1-B] OXAZOLE DERIVATIVES

TECHNICAL FIELD

The present invention relates to pharmaceutical compositions.

BACKGROUND ART 2,3-dihydro-6-nitroimidazo[2,1-b]oxazole compounds represented by general formula (1) shown below, optically active isomers thereof, and pharmacologically acceptable salts thereof (all of which are simply referred to as "oxazole compounds" below) are known to exhibit excellent bactericidal effects against *mycobacterium tuberculosis*, multidrug-resistant tubercle bacilli, and atypical acid-fast bacteria (see Japanese Unexamined Patent Publication No. 2004-149527 and WO 2005-042542): general formula (1):

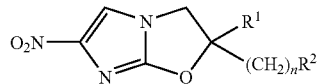

(1)

wherein $R^1$ represents a hydrogen atom or $C_{1-6}$ alkyl group; n represents an integer from 0 to 6; and $R^2$ represents any of the groups represented by general formulae (A) to (F) below:

groups represented by general formula (A):

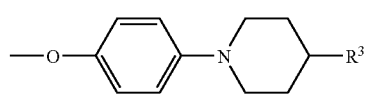

(A)

wherein $R^3$ represents any of the groups (1) to (6) shown below:

(1) phenoxy groups, optionally substituted on the phenyl ring with one or more members selected from the group consisting of halogen atoms, halo-substituted or unsubstituted $C_{1-6}$ alkyl groups, and halo-substituted or unsubstituted $C_{1-6}$ alkoxy groups;

(2) phenyl $C_{1-6}$ alkoxy groups, optionally substituted on the phenyl ring with one or more members selected from the group consisting of halogen atoms, halo-substituted or unsubstituted $C_{1-6}$ alkyl groups, and halo-substituted or unsubstituted $C_{1-6}$ alkoxy groups;

(3) —$NR^4R^5$ groups, wherein $R^4$ represents a $C_{1-6}$ alkyl group, and $R^5$ represents a phenyl group, optionally substituted on the phenyl ring with one or more members selected from the group consisting of halogen atoms, halo-substituted or unsubstituted $C_{1-6}$ alkyl groups, and halo-substituted or unsubstituted $C_{1-6}$ alkoxy groups;

(4) phenyl $C_{1-6}$ alkyl groups, optionally substituted on the phenyl ring with one or more members selected from the group consisting of halogen atoms, halo-substituted or unsubstituted $C_{1-6}$ alkyl groups, and halo-substituted or unsubstituted $C_{1-6}$ alkoxy groups;

(5) phenoxy $C_{1-6}$ alkyl groups, optionally substituted on the phenyl ring with one or more members selected from the group consisting of halogen atoms, halo-substituted or unsubstituted alkyl groups, and halo-substituted or unsubstituted $C_{1-6}$ alkoxy groups; and (6) benzofuryl $C_{1-6}$ alkyl groups, optionally substituted on the benzofuran ring with one or more members selected from the group consisting of halogen atoms, halo-substituted or unsubstituted alkyl groups, and halo-substituted or unsubstituted $C_{1-6}$ alkoxy groups;

groups represented by general formula (B):

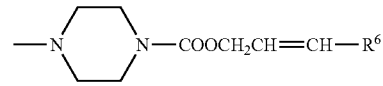

(B)

wherein $R^6$ represents a phenyl group, optionally substituted on the phenyl ring with one or more members selected from the group consisting of halogen atoms, halo-substituted or unsubstituted $C_{1-6}$ alkyl groups, and halo-substituted or unsubstituted $C_{1-6}$ alkoxy groups;

groups represented by general formula (C):

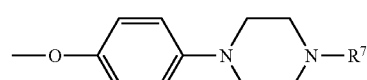

(C)

wherein $R^7$ represents a phenyl $C_{2-10}$ alkenyl group, optionally substituted on the phenyl ring with one or more members selected from the group consisting of halogen atoms, halo-substituted or unsubstituted $C_{1-6}$ alkyl groups, and halo-substituted or unsubstituted $C_{1-6}$ alkoxy groups, or represents a biphenyl $C_{1-6}$ alkyl group, optionally substituted on one or both phenyl rings with one or more members selected from the group consisting of halogen atoms, halo-substituted or unsubstituted $C_{1-6}$ alkyl groups, and halo-substituted or unsubstituted $C_{1-6}$ alkoxy groups;

groups represented by general formula (D):

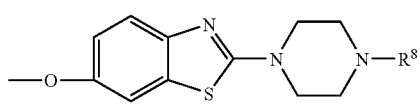

(D)

wherein $R^8$ represents a phenyl $C_{1-6}$ alkyl group, optionally substituted on the phenyl ring with one or more members selected from the group consisting of halogen atoms, halo-substituted or unsubstituted $C_{1-6}$ alkyl groups, and halo-substituted or unsubstituted $C_{1-6}$ alkoxy groups;

groups represented by general formula (E):

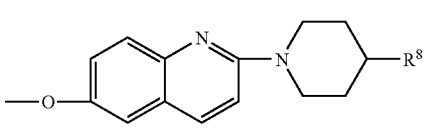

(E)

wherein $R^8$ is the same as above; and
groups represented by general formula (F):

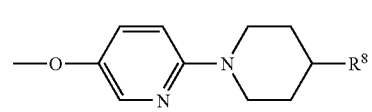

(F)

wherein $R^8$ is the same as above.

The oxazole compounds represented by general formula (1) above have low solubilities in water, and hence there is a demand for improvements in their solubilities.

DISCLOSURE OF THE INVENTION

Problem to be Solved by the Invention

An object of the present invention is to provide a pharmaceutical composition wherein the water solubility of an oxazole compound shown above is improved.

Means for Solving the Problem

The present inventors carried out extensive research to overcome the aforementioned problem, and found that the water solubilities of oxazole compounds can be substantially improved by adding thereto a particular cellulose compound, so as to yield desired pharmaceutical compositions. The present invention has been accomplished based on this finding.

The present invention provides pharmaceutical compositions as shown in Items 1 to 15 below:

Item 1. A pharmaceutical composition comprising:
(I) at least one oxazole compound selected from the group consisting of 2,3-dihydro-6-nitroimidazo[2,1-b]oxazole compounds represented by general formula (1), optically active isomers thereof, and pharmacologically acceptable salts thereof: general formula (1):

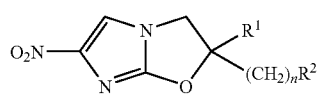

(1)

wherein $R^1$ represents a hydrogen atom or $C_{1-6}$ alkyl group; n represents an integer from 0 to 6; and $R^2$ represents any of the groups of general formulae (A) to (F) below:

groups represented by general formula (A):

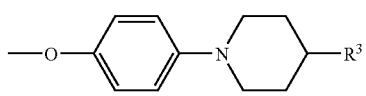

(A)

wherein $R^3$ represents any of the groups (1) to (6) shown below:

(1) phenoxy groups, optionally substituted on the phenyl ring with one or more members, preferably from 1 to 3, selected from the group consisting of halogen atoms, halo-substituted or unsubstituted $C_{1-6}$ alkyl groups, and halo-substituted or unsubstituted $C_{1-6}$ alkoxy groups;

(2) phenyl $C_{1-6}$ alkoxy groups, optionally substituted on the phenyl ring with one or more members, preferably from 1 to 3, selected from the group consisting of halogen atoms, halo-substituted or unsubstituted $C_{1-6}$ alkyl groups, and halo-substituted or unsubstituted $C_{1-6}$ alkoxy groups;

(3) —$NR^4R^5$ groups, wherein $R^4$ represents a $C_{1-6}$ alkyl group, and $R^5$ represents a phenyl group, optionally substituted on the phenyl ring with one or more members, preferably from 1 to 3, selected from the group consisting of halogen atoms, halo-substituted or unsubstituted $C_{1-6}$ alkyl groups, and halo-substituted or unsubstituted $C_{1-6}$ alkoxy groups;

(4) phenyl $C_{1-6}$ alkyl groups, optionally substituted on the phenyl ring with one or more members, preferably from 1 to 3, selected from the group consisting of halogen atoms, halo-substituted or unsubstituted $C_{1-6}$ alkyl groups, and halo-substituted or unsubstituted $C_{1-6}$ alkoxy groups;

(5) phenoxy $C_{1-6}$ alkyl groups, optionally substituted on the phenyl ring with one or more members, preferably from 1 to 3, selected from the group consisting of halogen atoms, halo-substituted or unsubstituted $C_{1-6}$ alkyl groups, and halo-substituted or unsubstituted $C_{1-6}$ alkoxy groups; and (6) benzofuryl $C_{1-6}$ alkyl groups, optionally substituted on the benzofuran ring with one or more members, preferably from 1 to 3, selected from the group consisting of halogen atoms, halo-substituted or unsubstituted $C_{1-6}$ alkyl groups, and halo-substituted or unsubstituted $C_{1-6}$ alkoxy groups;

groups represented by general formula (B):

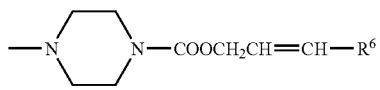

(B)

wherein $R^6$ represents a phenyl group, optionally substituted on the phenyl ring with one or more members, preferably from 1 to 3, selected from the group consisting of halogen atoms, halo-substituted or unsubstituted $C_{1-6}$ alkyl groups, and halo-substituted or unsubstituted $C_{1-6}$ alkoxy groups;

groups represented by general formula (C):

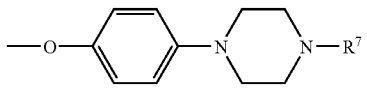

(C)

wherein $R^7$ represents a phenyl $C_{2-10}$ alkenyl group, optionally substituted on the phenyl ring with one or more members, preferably from 1 to 3, selected from the group consisting of halogen atoms, halo-substituted or unsubstituted $C_{1-6}$ alkyl groups, and halo-substituted or unsubstituted $C_{1-6}$ alkoxy groups, or represents a biphenyl $C_{1-6}$ alkyl group, optionally substituted on one or both phenyl rings with one or more members, preferably from 1 to 3, selected from the group consisting of halogen atoms, halo-substituted or unsubstituted alkyl groups, and halo-substituted or unsubstituted $C_{1-6}$ alkoxy groups;

groups represented by general formula (D):

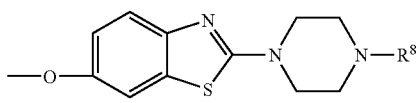

(D)

wherein $R^8$ represents a phenyl $C_{1-6}$ alkyl group, optionally substituted on the phenyl ring with one or more members, preferably from 1 to 3, selected from the group consisting of halogen atoms, halo-substituted or unsubstituted $C_{1-6}$ alkyl groups, and halo-substituted or unsubstituted $C_{1-6}$ alkoxy groups;

groups represented by general formula (E):

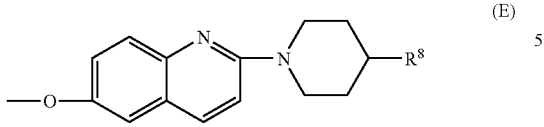

wherein R⁸ is the same as above; and
groups represented by general formula (F):

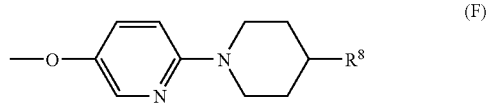

wherein R⁸ is the same as above; and (II) at least one cellulose compound selected from the group consisting of hydroxypropyl methylcellulose phthalate and hydroxypropyl methylcellulose acetate succinate.

Item 2. A pharmaceutical composition according to Item 1, wherein the oxazole compound is 2-methyl-6-nitro-2-{4-[4-(4-trifluoromethoxyphenoxy)piperidin-1-yl]phenoxymethyl}-2,3-dihydroimidazo[2,1-b]oxazole.

Item 3. A pharmaceutical composition according to Item 1, wherein the oxazole compound is 6-nitro-2-{4-[4-(4-trifluoromethoxybenzyloxy)piperidine-1-yl]phenoxymethyl}-2,3-dihydroimidazo[2,1-b]oxazole.

Item 4. A pharmaceutical composition according to Item 1, wherein the oxazole compound is 2-methyl-6-nitro-2-(4-{4-[3-(4-trifluoromethoxyphenyl)-2-propenyl]piperazin-1-yl}phenoxymethyl)-2,3-dihydroimidazo[2,1-b]oxazole.

Item 5. A pharmaceutical composition according to Item 1, wherein the oxazole compound is 2-methyl-6-nitro-2-{4-[4-(4-trifluoromethylphenoxymethyl)piperidin-1-yl]phenoxymethyl}-2,3-dihydroimidazo[2,1-b]oxazole.

Item 6. A pharmaceutical composition according to Item 1, further comprising vitamin E.

Item 7. A pharmaceutical composition according to Item 6, wherein the vitamin E is dl-α-tocopherol.

Item 8. A pharmaceutical composition according to Item 2, further comprising vitamin E.

Item 9. A pharmaceutical composition according to Item 8, wherein the vitamin E is dl-α-tocopherol.

Item 10. A pharmaceutical composition according to Item 3, further comprising vitamin E.

Item 11. A pharmaceutical composition according to Item 10, wherein the vitamin E is dl-α-tocopherol.

Item 12. A pharmaceutical composition according to Item 4, further comprising vitamin E.

Item 13. A pharmaceutical composition according to Item 12, wherein the vitamin E is dl-α-tocopherol.

Item 14. A pharmaceutical composition according to Item 5, further comprising vitamin E.

Item 15. A pharmaceutical composition according to Item 14, wherein the vitamin E is dl-α-tocopherol.

The oxazole compound used in the pharmaceutical composition of the present invention is a 2,3-dihydro-6-nitroimidazo[2,1-b]oxazole compound represented by general formula (I) shown above.

Oxazole compounds represented by general formula (1) above encompass the following compounds:

2-methyl-6-nitro-2-{4-[4-(4-trifluoromethoxyphenoxy)piperidin-1-yl]phenoxymethyl}-2,3-dihydroimidazo[2,1-b]oxazole (hereinafter "compound A");

4-(2-methyl-6-nitro-2,3-dihydroimidazo[2,1-b]oxazol-2-ylmethyl)piperazine-1-carboxylic acid 3-(4-trifluoromethylphenyl)-2-propenylester (hereinafter "compound B");

2-(4-{4-[N-(4-chlorophenyl)-N-methyl-amino]piperidin-1-yl}phenoxymethyl)-2-methyl-6-nitro-2,3-dihydroimidazo[2,1-b]oxazole (hereinafter "compound C");

2-methyl-6-nitro-2-{4-[4-(4-trifluoromethoxybenzyl)piperidin-1-yl]phenoxymethyl}-2,3-dihydroimidazo[2,1-b]oxazole (hereinafter "compound D");

2-{4-[4-(3,4-dichlorobenzyl)piperidin-1-yl]phenoxymethyl}-2-methyl-6-nitro-2,3-dihydroimidazo[2,1-b]oxazole (hereinafter "compound E");

6-nitro-2-{4-[4-(4-trifluoromethoxyphenoxy)piperidin-1-yl]phenoxymethyl}-2,3-dihydroimidazo[2,1-b]oxazole (hereinafter "compound F");

6-(2-methyl-6-nitro-2,3-dihydroimidazo[2,1-b]oxazole-2-ylmethoxy)-2-[4-(4-trifluoromethoxyphenoxy)piperazin-1-yl]benzothiazole (hereinafter "compound G");

6-nitro-2-{4-[4-(4-trifluoromethoxybenzyloxy)piperidine-1-yl]phenoxymethyl}-2,3-dihydroimidazo[2,1-b]oxazole (hereinafter "compound H");

2-methyl-6-nitro-2-(4-{4-[2-(4-trifluoromethoxyphenyl)ethyl]piperidin-1-yl}phenoxymethyl)-2,3-dihydroimidazo[2,1-b]oxazole (hereinafter "compound I");

2-{4-[4-(4-chlorophenoxymethyl)piperidin-1-yl]phenoxymethyl}-2-methyl-6-nitro-2,3-dihydroimidazo[2,1-b]oxazole (hereinafter "compound J");

6-nitro-2-{4-[4-(4-trifluoromethoxyphenoxymethyl)piperidin-1-yl]phenoxymethyl}-2,3-dihydroimidazo[2,1-b]oxazole (hereinafter "compound K");

6-nitro-2-{4-[4-(4-trifluoromethoxybenzyl)piperidin-1-yl]phenoxymethyl}-2,3-dihydroimidazo[2,1-b]oxazole (hereinafter "compound L");

2-methyl-6-nitro-2-{4-[4-(4-trifluoromethoxybenzyloxy)piperidin-1-yl]phenoxymethyl}-2,3-dihydroimidazo[2,1-b]oxazole (hereinafter "compound M");

2-methyl-6-nitro-2-(4-{4-[3-(4-trifluoromethoxyphenyl)-2-propenyl]piperazin-1-yl}phenoxymethyl)-2,3-dihydroimidazo[2,1-b]oxazole (hereinafter "compound N");

2-{4-[4-(4-chlorophenoxymethyl)piperidin-1-yl]phenoxymethyl}-6-nitro-2,3-dihydroimidazo[2,1-b]oxazole (hereinafter "compound O");

6-nitro-2-{4-[4-(4-trifluoromethylphenoxymethyl)piperidin-1-yl]phenoxymethyl}-2,3-dihydroimidazo[2,1-b]oxazole (hereinafter "compound P");

2-methyl-6-nitro-2-{4-[4-(4-trifluoromethylphenoxymethyl)piperidin-1-yl]phenoxymethyl}-2,3-dihydroimidazo[2,1-b]oxazole (hereinafter "compound Q");

2-methyl-6-nitro-2-{4-[4-(4-trifluoromethoxyphenoxymethyl)piperidin-1-yl]phenoxymethyl}-2,3-dihydroimidazo[2,1-b]oxazole (hereinafter "compound R");

6-nitro-2-(4-{4-[3-(4-trifluoromethoxyphenyl)propyl]piperidin-1-yl}phenoxymethyl)-2,3-dihydroimidazo[2,1-b]oxazole (hereinafter "compound S");

5-(2-methyl-6-nitro-2,3-dihydroimidazo[2,1-b]oxazol-2-ylmethoxy)-2-[4-(4-trifluoromethoxybenzyl)piperidin-1-yl]pyridine (hereinafter "compound T");

2-methyl-6-nitro-2-{4-[4-(5-trifluoromethylbenzofuran-2-ylmethyl)piperidin-1-yl]phenoxymethyl}-2,3-dihydroimidazo[2,1-b]oxazole (hereinafter "compound U");

6-(2-methyl-6-nitro-2,3-dihydroimidazo[2,1-b]oxazol-2-yl-methoxy)-2-[4-(4-trifluoromethoxybenzyl)piperidin-1-yl]quinoline (hereinafter "compound V"); and 6-nitro-2-{4-[4-(4'-trifluoromethylbiphenyl-4-ylmethyl)piperazin-1-yl]phenoxymethyl}-2,3-dihydroimidazo[2,1-b]oxazole (hereinafter "compound W").

In the present invention, at least one member is preferably used selected from the group consisting of the aforementioned oxazole compounds, optically active isomers thereof, and pharmacologically acceptable salts thereof.

Optically active isomers of the oxazole compounds encompass those in the R- and S-configurations.

Examples of pharmacologically acceptable salts include hydrochlorides, citrates, succinates, fumarates, and the like.

A preferred oxazole compound is at least one member selected from the group consisting of compound A, compound H, compound N, and compound Q as well as optically active isomers and pharmacologically acceptable salts thereof.

The cellulose compound used in the present pharmaceutical composition is at least one member selected from the group consisting of hydroxypropyl methylcellulose phthalate and hydroxypropyl methylcellulose acetate succinate. The addition of such a cellulose compound allows the water solubility of the oxazole compound to be remarkably improved.

Hydroxypropyl methylcellulose phthalate is a polymer resulting from half-esterifying phthalic acid with hydroxypropyl cellulose. Hydroxypropyl methylcellulose phthalate is a known compound, and, for example, is available from Shin-Etsu Chemical Co., Ltd. under the trade names HP-55, HP-55S and HP-50. Any of these commercial products can be used in the present invention. Hydroxypropyl methylcellulose phthalate is substituted at the hydroxyl groups with 18 to 24% of methoxy groups; 5 to 10% of hydroxypropoxy groups; and 21 to 35% of carboxybenzoyl groups.

Hydroxypropyl methylcellulose acetate succinate is a polymer resulting from esterifying acetic acid and succinic acid with hydroxypropyl cellulose. Hydroxypropyl methylcellulose acetate succinate is a known compound, and, for example, is available from Shin-Etsu Chemical Co., Ltd. under the trade names AS-L, AS-M, and AS-H. Any of these commercial products can be used in the present invention. Hydroxypropyl methylcellulose acetate succinate is substituted at the hydroxyl groups with 20 to 26% of methoxy groups; 5 to 10% of hydroxypropyl groups; 5 to 14% of acetyl groups; and 4 to 18% of succinoyl groups.

Among the aforementioned cellulose compounds, those which are soluble in pH 5 to 5.5 McIlvaine buffer solutions are preferable. Such cellulose compounds include the products HP-55, HP-55S, HP-50, and AS-L.

Among such cellulose compounds, those which are soluble in pH 5 McIlvaine buffer solutions are especially preferable. Such cellulose compounds include the product HP-50.

In order to achieve the excellent effects of the present invention, the proportion of ingredient (II) to ingredient (I) in the present pharmaceutical composition is such that ingredient (II) is typically used in an amount of about 0.5 part by weight or more, preferably about 1 part by weight or more, and more preferably about 1.5 parts by weight or more, per part by weight of ingredient (I). In consideration of the dosage forms of present pharmaceutical compositions, ingredient (II) is typically used in an amount of about 15 parts by weight or less, preferably about 10 parts by weight or less, more preferably about 5 parts by weight or less, and still more preferably about 3 parts by weight or less, per part by weight of ingredient (I).

The pharmaceutical composition may further include vitamin E.

Examples of forms of vitamin E include natural and synthetic forms of vitamin E, such as d-α-tocopherol, d-δ-tocopherol, d-α-tocopherol acetate, d-α-tocopherol succinate, dl-α-tocopherol, dl-α-tocopherol acetate, dl-α-tocopherol succinate, dl-α-tocopherol calcium succinate, dl-α-tocopherol nicotinate, and the like. Preferable forms of vitamin E are dl-α-tocopherol, dl-α-tocopherol acetate, dl-α-tocopherol succinate, and dl-α-tocopherol nicotinate; and dl-α-tocopherol is especially preferable.

The present pharmaceutical composition preferably includes vitamin E. The addition of vitamin E allows the stability of the pharmaceutical composition to be remarkably improved. When compounds with similar antioxidant effects to vitamin E are used instead of vitamin E, such as dibutylhydroxytoluene, butylhydroxyanisole, soybean lecithin, ascorbyl palmitate, cysteine hydrochloride, ascorbic acid, citric acid, erythorbic acid, sodium nitrite, sodium sulfite, sodium thioglycolate, sodium thiomalate, and the like, the stability of the pharmaceutical composition cannot be remarkably improved, which is a fact discovered by the present inventors.

The addition of such vitamin E, particularly dl-α-tocopherol, remarkably enhances the stability of the pharmaceutical composition without adversely affecting the water solubility of the oxazole compound.

The amount of vitamin E added to the pharmaceutical composition is usually from about 0.001 to about 1 part by weight, preferably from about 0.01 to about 0.8 part by weight, and more preferably from about 0.03 to about 0.5 part by weight, per part by weight of ingredient (I).

The pharmaceutical composition of the present invention may further comprise a variety of suitable auxiliary ingredients, such as pH-independent water-soluble polymers, plasticizers and the like.

Examples of pH-independent water-soluble polymers include hydroxypropyl cellulose, hydroxypropyl methylcellulose, polyvinylpyrrolidone, polyethylene glycol, cyclodextrins, and the like.

Examples of plasticizers include triethyl citrate, glycerol, glycerol fatty acid esters, medium-chain triglycerides, triacetin, castor oil, propylene glycol, polysorbates, and the like.

The pharmaceutical composition of the present invention may be made into the form of a typical pharmaceutical preparation by a known method, using carriers such as excipients, disintegrants, binders, fluidizers, lubricants, coating agents, coloring agents, suspending agents, sweetening agents and surfactants, as needed. Pharmaceutical preparation forms include, for example, powders, tablets, pills, capsules, and the like.

Examples of excipients include lactose, anhydrous lactose, refined sugar, white sugar, D-mannitol, D-sorbitol, xylitol, erythritol, dextrin, crystalline cellulose, microcrystalline cellulose, corn starch, potato starch, anhydrous calcium hydrogenphosphate, and the like.

Examples of disintegrants include sodium carboxymethyl starch, carmellose, carmellose calcium, carmellose sodium, croscarmellose sodium, crospovidone, low-substituted hydroxypropylcellulose, partially pregelatinized starch, and the like.

Examples of binders include hydroxypropyl cellulose, hydroxypropyl methylcellulose, polyvinyl pyrrolidone, pregelatinized starch, syrups, starch syrup, and the like.

Examples of fluidizers include light anhydrous silicic acid, synthetic aluminium silicates, hydrated silicon dioxide, calcium stearate, magnesium metasilicate aluminate, talc, and the like.

Examples of lubricants include magnesium stearate, calcium stearate, magnesium silicate, magnesium oxide, talc, hydrogenated oil, sucrose fatty acid esters, sodium stearyl fumarate, and the like.

Examples of coating agents include hydroxypropyl methylcellulose, polyvinyl alcohol, polysorbates, macrogol, talc, and the like.

Examples of coloring agents include yellow ferric oxide, brown iron oxide, red ferric oxide, titanium oxide, Food Blue No. 1, Food Red No. 2, Food Red No. 3, Food Yellow No. 4, and the like.

Examples of suspending agents include polysorbates, polyethylene glycol, gum arabic, glycerol, gelatin, and the like.

Examples of sweetening agents include aspartame, saccharin, saccharin sodium, starch syrup, fructose, and the like.

Examples of surfactants include sodium lauryl sulfate, polysorbates, polyoxyethylene hydrogenated castor oil, and the like.

Capsules may be prepared in accordance with a known process by mixing ingredients (I), (II) and the like with any of the aforementioned carriers, and charging such a mixture into hard capsules made from gelatin, hydroxypropyl methylcellulose, polyvinyl alcohol, and the like, or into gelatin-based soft capsules.

EFFECTS OF THE INVENTION

The present invention allows the water solubility of an oxazole compound to be substantially improved by adding hydroxypropyl methylcellulose phthalate and/or hydroxypropyl methylcellulose acetate succinate to the oxazole compound. Thus, a pharmaceutical composition is provided wherein the water solubility of an oxazole compound is improved. The stability of such a pharmaceutical composition can be remarkably improved by further adding vitamin E to the oxazole compound and aforementioned cellulose compound(s).

BEST MODE FOR CARRYING OUT THE INVENTION

Figure 1:
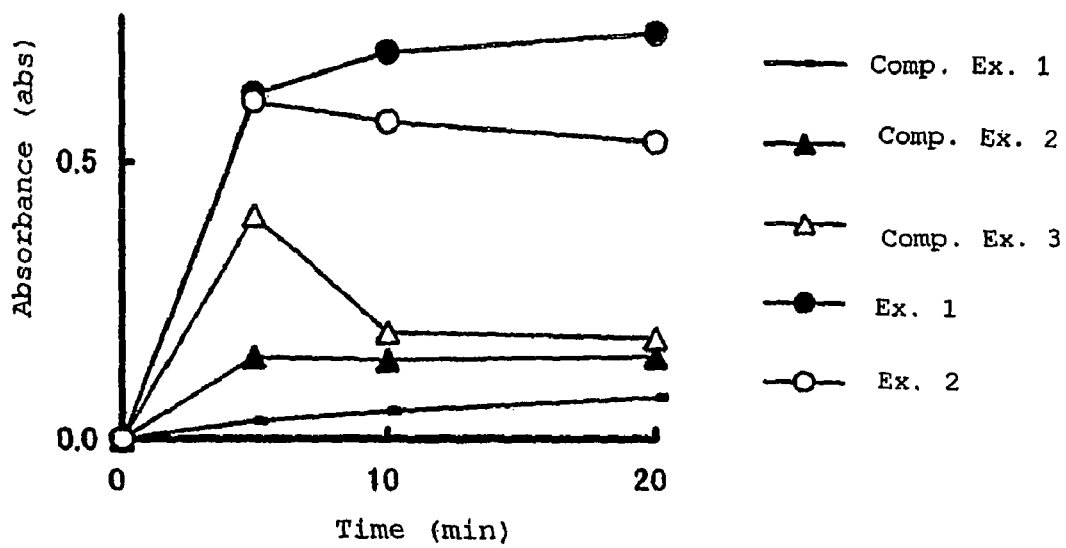
FIG. 1 is a graph which shows the relationship between time and the absorbance of solutions containing the pharmaceutical composition obtained in Example 1 or 2, or Comparative Example 1, 2 or 3.

The present invention will become more apparent by reference to the following Examples.

Formulation Example 1

| | |
|---|---|
| Compound A | 50 mg |
| Hydroxypropyl methylcellulose phthalate (HP-50, manufactured by Shin-Etsu Chemical Co., Ltd.) | 150 mg |
| Lactose (SuperTab HP-01, manufactured by Lactose Company of NZ) | 100 mg |
| Crystalline cellulose (CEOLUS PH 301, manufactured by Asahi Kasei Corporation) | 100 mg |
| Sodium carboxymethyl starch (Primogel, manufactured by DMV) | 40 mg |
| Carmellose calcium (E. C. G.-505, manufactured by Gotoku Chemical Company Ltd.) | 40 mg |
| Light anhydrous silicic acid (Adsolider 101, manufactured by Freund Corporation) | 6 mg |
| Magnesium stearate (manufactured by Taihei Chemical Industrial Co., Ltd.) | 6 mg |

Tablets were formulated which contain the aforementioned contents of ingredients per tablet.

Formulation Example 2

| | |
|---|---|
| Compound A | 50 mg |
| Hydroxypropyl methylcellulose phthalate (HP-50, manufactured by Shin-Etsu Chemical Co., Ltd.) | 150 mg |
| Light anhydrous silicic acid (Adsolider 101, manufactured by Freund Corporation) | 20 mg |

Capsules were formulated which contain the aforementioned contents of ingredients per capsule.

Example 1

1 g of compound A (R-configuration) and 3 g of hydroxypropyl methylcellulose phthalate (HP-50, manufactured by Shin-Etsu Chemical Co., Ltd.) were dissolved in 100 ml of a methylene chloride/ethanol mixture (methylene chloride:ethanol=8:2 by weight). The mixture was then spray dried with a spray dryer (GS-310, manufactured by Yamato Scientific Co., Ltd.). The resulting spray dried product was further dried at 60° C. for more than 12 hours using a vacuum dryer (LCV-323, manufactured by Tabai Espec Corp.), so as to yield a pharmaceutical composition of the present invention in powder form.

Example 2

A pharmaceutical composition of the present invention in powder form was formulated as in Example 1, except for using hydroxypropyl methylcellulose acetate succinate (AS-L, manufactured by Shin-Etsu Chemical Co., Ltd.) instead of hydroxypropyl methylcellulose phthalate.

Comparative Example 1

1 g of compound A (R-configuration) was ground using a jet mill (A-O, SEISHIN ENTERPRISE CO., LTD), so as to give a pharmaceutical composition for comparison.

Comparative Example 2

A pharmaceutical composition in powder form was formulated as in Example 1, except for using hydroxypropyl cellulose (HPC-SL, Nippon Soda Co., LTD.) instead of hydroxypropyl methylcellulose phthalate.

Comparative Example 3

A pharmaceutical composition in powder form was formulated as in Example 1, except for using hydroxypropyl cellulose (TC-5E, Nippon Soda Co., LTD.) instead of hydroxypropyl methylcellulose phthalate.

Test Example 1

The solubilities of the pharmaceutical compositions obtained in Examples 1 and 2 and Comparative Examples 1 to 3 were examined as follows.

First, 100 ml of a 0.3 wt % aqueous sodium lauryl sulfate solution was poured into a 100 ml beaker, and was stirred with a magnetic stirrer (number of revolutions: 500 rpm). Separately, one of each of the aforementioned pharmaceutical compositions was weighed to contain 5 mg of compound A, and was placed into an agate mortar, after which a few ml of the test solution in the beaker was added to the pharmaceutical composition. After dispersion for about 1 minute, the mixture was poured into the beaker. After 5, 10 and 20 minutes from pouring the dispersion in the beaker, 6 ml of the solution in the beaker was sampled, and was filtered through a membrane filter with a pore diameter of 0.5 μm or less. The initial 2 ml of each filtrate was removed, and the subsequent 4 ml was used as a sample solution.

The absorbance of each sample solution at a wavelength of 335 nm was measured by UV visible absorbance spectroscopy using a 10 mm long cell.

The results are shown in FIG. 1.

FIG. 1 shows that the water solubilities of the pharmaceutical compositions obtained in Examples 1 and 2 are remarkably improved.

Example 3

A pharmaceutical composition of the present invention in powder form was formulated as in Example 1, except for using 2 g of hydroxypropyl methylcellulose phthalate instead of 3 g of hydroxypropyl methylcellulose phthalate.

Example 4

A pharmaceutical composition of the present invention in powder form was formulated as in Example 1, except for using 1.5 g of hydroxypropyl methylcellulose phthalate instead of 3 g of hydroxypropyl methylcellulose phthalate.

The water solubilities of the pharmaceutical compositions obtained in Examples 3 and 4 were also examined as in Test Example 1. As a result, the water solubilities of these pharmaceutical compositions were found to be on the same level as that of the pharmaceutical composition in Example 1. The results reveal that the effect of the present invention is obtainable in all of the cases in which the amount of hydroxypropyl methylcellulose phthalate varied in the range of 1.5 to 3 g per g of compound A.

Example 5

1 g of compound Q (R-configuration) and 3 g of hydroxypropyl methylcellulose phthalate (HP-50, manufactured by Shin-Etsu Chemical Co., Ltd.) were dissolved in 100 ml of a methylene chloride/ethanol mixture (methylene chloride:ethanol=8:2 by weight). The mixture was then spray dried with a spray dryer (GS-310, manufactured by Yamato Scientific Co., Ltd.). The resulting spray dried product was further dried at 60° C. for more than 12 hours using a vacuum dryer (LCV-323, manufactured by Tabai Espec Corp.), so as to yield a pharmaceutical composition of the present invention in powder form.

Comparative Example 4

1 g of compound Q (R-configuration) was ground with a jet mill (A-O, manufactured by SEISHIN ENTERPRISE CO., LTD), so as to give a pharmaceutical composition for comparison.

Comparative Example 5

A pharmaceutical composition in powder form was prepared as in Example 5, except for using hydroxypropyl cellulose (HPC-SL, manufactured by Nippon Soda Co., Ltd.) instead of hydroxypropyl methylcellulose phthalate.

Test Example 2

The solubilities of the pharmaceutical compositions obtained in Example 5, Comparative Example 4, and Comparative Example 5 were examined as in Test Example 1.

Figure 2:
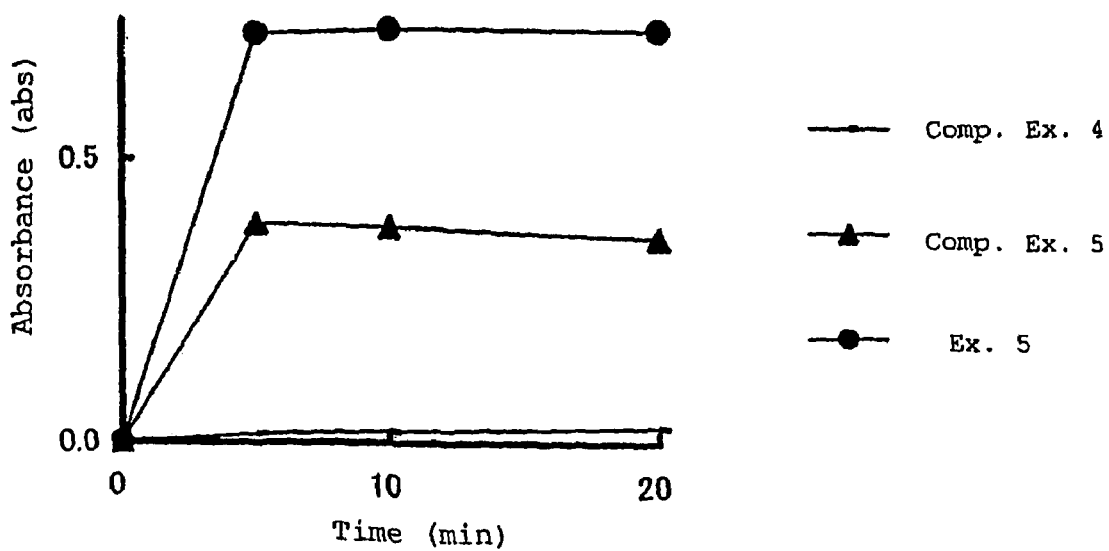
FIG. 2 is a graph which shows the relationship between time and the absorbance of solutions containing the pharmaceutical composition obtained in Example 5 or Comparative Example 4 or 5.

The results are shown in FIG. 2.

FIG. 2 shows that the water solubility of the pharmaceutical composition of Example 5 is remarkably improved.

Example 6

2 g of compound A (R-configuration), 3 g of hydroxypropyl methylcellulose phthalate (HP-50, manufactured by Shin-Etsu Chemical Co., Ltd.), and 0.08 g of dl-α-tocopherol (anti-oxidizing agent, manufactured by Wako Pure Chemical Industries, Ltd.) were dissolved in 100 ml of a methylene chloride/ethanol mixture (methylene chloride:ethanol=8:2 by weight). The mixture was then spray dried with a spray dryer (GS-310, manufactured by Yamato Scientific Co., Ltd.). The resulting spray dried product was further dried at 60° C. for more than 12 hours with a vacuum dryer (LCV-323, manufactured by Tabai Espec Corp.), so as to yield a pharmaceutical composition of the invention in powder form.

Example 7

A pharmaceutical composition of the invention in powder form was prepared as in Example 6, except for using 0.04 g of dibutylhydroxytoluene (anti-oxidizing agent) instead of dl-α-tocopherol.

Example 8

A pharmaceutical composition of the invention in powder form was prepared as in Example 6, except for using 0.004 g of butylhydroxyanisole (anti-oxidizing agent) instead of dl-α-tocopherol.

Example 9

A pharmaceutical composition of the invention in powder form was prepared as in Example 6, except for not using an anti-oxidizing agent.

Test Example 3

After keeping the pharmaceutical compositions obtained in Examples 6 to 9 at 40° C. for a week, the purity of compound A contained in each composition was examined. The purity of compound A was determined by area percent.

The results are shown in Table 1 below.

TABLE 1

| | Purity of Compound A | |
|---|---|---|
| | Prior to Testing | After 1 Week at 40° C. |
| Example 6 | 98.3% | 97.6% |
| Example 7 | 98.3% | 90.7% |
| Example 8 | 98.0% | 68.8% |
| Example 9 | 97.8% | 66.9% |

Table 1 shows that the stability of compound A is significantly improved by the addition of dl-α-tocopherol.

Example 10

A pharmaceutical composition of the invention in powder form was prepared as in Example 1, except for using 1 g of compound B (R-configuration) instead of compound A (R-configuration).

Example 11

A pharmaceutical composition of the invention in powder form was prepared as in Example 1, except for using 1 g of compound C(R-configuration) instead of compound A (R-configuration).

Example 12

A pharmaceutical composition of the invention in powder form was prepared as in Example 1, except for using 1 g of compound D (R-configuration) instead of compound A (R-configuration).

Example 13

A pharmaceutical composition of the invention in powder form was prepared as in Example 1, except for using 1 g of compound G (R-configuration) instead of compound A (R-configuration).

Example 14

A pharmaceutical composition of the invention in powder form was prepared as in Example 1, except for using 1 g of compound H(R-configuration) instead of compound A (R-configuration).

Example 15

A pharmaceutical composition of the invention in powder form was prepared as in Example 1, except for using 1 g of compound N(R-configuration) instead of compound A (R-configuration).

Example 16

A pharmaceutical composition of the invention in powder form was prepared as in Example 1, except for using 1 g of compound T (R-configuration) instead of compound A (R-configuration).

Example 17

A pharmaceutical composition of the invention in powder form was prepared as in Example 1, except for using 1 g of compound U (R-configuration) instead of compound A (R-configuration).

Example 18

A pharmaceutical composition of the invention in powder form was prepared as in Example 1, except for using 1 g of compound V (R-configuration) instead of compound A (R-configuration).

Test Example 3

The solubilities of the pharmaceutical compositions obtained in Examples 10 to 18 were examined in the same manner as Test Example 1. The results revealed that the compositions obtained in Examples 10 to 18 all possess remarkably improved solubilities in water.

The invention claimed is:

1. A pharmaceutical composition comprising:
   (I) at least one oxazole compound selected from the group consisting of 2,3-dihydro-6-nitroimidazo[2,1-b]oxazole compounds represented by general formula (1), optically active isomers thereof, and pharmacologically acceptable salts thereof: general formula (1):

$$O_2N \text{—} \underset{N}{\overset{N}{\diagdown}} \text{—} \overset{R^1}{\underset{O}{\diagdown}} (CH_2)_n R^2 \quad (1)$$

wherein $R^1$ represents a hydrogen atom or $C_{1-6}$ alkyl group; n represents an integer from 0 to 6; and $R^2$ represents any of the groups of general formula (A) to (F) below:

groups represented by general formula (A):

$$\text{—O—} \bigcirc \text{—N} \bigcirc \text{—} R^3 \quad (A)$$

wherein $R^3$ represents any of the groups (1) to (6) shown below:

(1) phenoxy groups, optionally substituted on the phenyl ring with one or more members selected from the group consisting of halogen atoms, halo-substituted or unsubstituted $C_{1-6}$ alkyl groups, and halo-substituted or unsubstituted $C_{1-6}$ alkoxy groups;

(2) phenyl $C_{1-6}$ alkoxy groups, optionally substituted on the phenyl ring with one or more members selected from the group consisting of halogen atoms, halo-substituted or unsubstituted $C_{1-6}$ alkyl groups, and halo-substituted or unsubstituted $C_{1-6}$ alkoxy groups;

(3) —$NR^4R^5$ groups, wherein $R^4$ represents a $C_{1-6}$ alkyl group, and $R^5$ represents a phenyl group, optionally substituted on the phenyl ring with one or more members selected from the group consisting of halogen atoms, halo-substituted or unsubstituted $C_{1-6}$ alkyl groups, and halo-substituted or unsubstituted $C_{1-6}$ alkoxy groups;

(4) phenyl $C_{1-6}$ alkyl groups, optionally substituted on the phenyl ring with one or more members selected from the group consisting of halogen atoms, halo-substituted or unsubstituted alkyl groups, and halo-substituted or unsubstituted $C_{1-6}$ alkoxy groups;

(5) phenoxy $C_{1-6}$ alkyl groups, optionally substituted on the phenyl ring with one or more members selected from the group consisting of halogen atoms, halo-substituted or unsubstituted $C_{1-6}$ alkyl groups, and halo-substituted or unsubstituted $C_{1-6}$ alkoxy groups; and (6) benzofuryl $C_{1-6}$ alkyl groups, optionally substituted on the benzofuran ring with one or more members selected from the group consisting of halogen atoms, halo-substituted or unsubstituted $C_{1-6}$ alkyl groups, and halo-substituted or unsubstituted $C_{1-6}$ alkoxy groups;

groups represented by general formula (B):

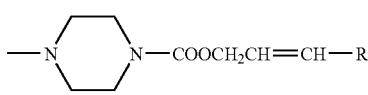

(B)

wherein $R^6$ represents a phenyl group, optionally substituted on the phenyl ring with one or more members selected from the group consisting of halogen atoms, halo-substituted or unsubstituted $C_{1-6}$ alkyl groups, and halo-substituted or unsubstituted $C_{1-6}$ alkoxy groups;

groups represented by general formula (C):

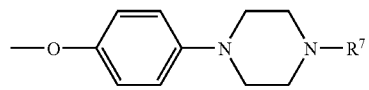

(C)

wherein $R^7$ represents a phenyl $C_{2-10}$ alkenyl group, optionally substituted on the phenyl ring with one or more members selected from the group consisting of halogen atoms, halo-substituted or unsubstituted $C_{1-6}$ alkyl groups, and halo-substituted or unsubstituted $C_{1-6}$ alkoxy groups, or represents a biphenyl $C_{1-6}$ alkyl group, optionally substituted on one or both phenyl rings with one or more members selected from the group consisting of halogen atoms, halo-substituted or unsubstituted $C_{1-6}$ alkyl groups, and halo-substituted or unsubstituted $C_{1-6}$ alkoxy groups;

groups represented by general formula (D):

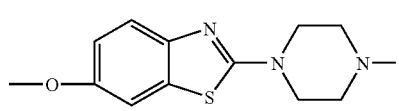

(D)

wherein $R^8$ represents a phenyl $C_{1-6}$ alkyl group, optionally substituted on the phenyl ring with one or more members selected from the group consisting of halogen atoms, halo-substituted or unsubstituted $C_{1-6}$ alkyl groups, and halo-substituted or unsubstituted $C_{1-6}$ alkoxy groups;

groups represented by general formula (E):

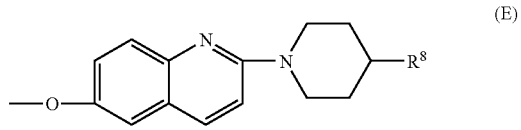

(E)

wherein $R^8$ is the same as above; and groups represented by general formula (F):

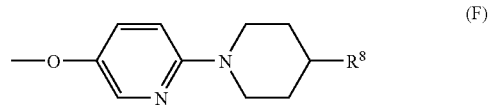

(F)

wherein $R^8$ is the same as above; and (II) at least one cellulose compound selected from the group consisting of hydroxypropyl methylcellulose phthalate and hydroxypropyl methylcellulose acetate succinate.

2. A pharmaceutical composition according to claim 1, wherein the oxazole compound is 2-methyl-6-nitro-2-{4-[4-(4-trifluoromethoxyphenoxy)piperidin-1-yl]phenoxymethyl}-2,3-dihydroimidazo[2,1-b]oxazole.

3. A pharmaceutical composition according to claim 1, wherein the oxazole compound is 6-nitro-2-{4-[4-(4-trifluoromethoxybenzyloxy)piperidine-1-yl]phenoxymethyl}-2,3-dihydroimidazo[2,1-b]oxazole.

4. A pharmaceutical composition according to claim 1, wherein the oxazole compound is 2-methyl-6-nitro-2-(4-{4-[3-(4-trifluoromethoxyphenyl)-2-propenyl]piperazin-1-yl}phenoxymethyl)-2,3-dihydroimidazo[2,1-b]oxazole.

5. A pharmaceutical composition according to claim 1, wherein the oxazole compound is 2-methyl-6-nitro-2-{4-[4-(4-trifluoromethylphenoxymethyl)piperidin-1-yl]phenoxymethyl}-2,3-dihydroimidazo[2,1-b]oxazole.

6. A pharmaceutical composition according to claim 1, further comprising vitamin E.

7. A pharmaceutical composition according to claim 6, wherein the vitamin E is dl-α-tocopherol.

8. A pharmaceutical composition according to claim 3, further comprising vitamin E.

9. A pharmaceutical composition according to claim 8, wherein the vitamin E is dl-α-tocopherol.

10. A pharmaceutical composition according to claim 4, further comprising vitamin E.

11. A pharmaceutical composition according to claim 10, wherein the vitamin E is dl-α-tocopherol.

12. A pharmaceutical composition according to claim 2, wherein the oxazole compound is (R)-2-methyl-6-nitro-2-{4-[4-(4-trifluoromethoxyphenoxy)piperidin-1-yl]phenoxymethyl}-2,3-dihydroimidazo[2,1-b]oxazole.

13. A pharmaceutical composition according to claim 5, wherein the oxazole compound is (R)-2-methyl-6-nitro-2-{4-[4-(4-trifluoromethylphenoxymethyl)piperidin-1-yl]phenoxymethyl}-2,3-dihydroimidazo[2,1-b]oxazole.

14. A pharmaceutical composition according to claim 2 or 12, further comprising vitamin E.

15. A pharmaceutical composition according to claim 14, wherein the vitamin E is dl-α-tocopherol.

16. A pharmaceutical composition according to claim 5 or 13, further comprising vitamin E.

17. A pharmaceutical composition according to claim 16, wherein the vitamin E is dl-α-tocopherol.

* * * * *